(12) United States Patent
Dawson et al.

(10) Patent No.: US 7,790,005 B2
(45) Date of Patent: Sep. 7, 2010

(54) ELECTRODE AND METHOD FOR MAKING ELECTRODE

(75) Inventors: Darryl Hirst Dawson, Braintree (GB);
William Joseph Yost, III, London (GB);
Christopher William Ogilvie Thompson, Alton (GB)

(73) Assignee: Element Six Limited, Ascot (GB)

( * ) Notice: Subject to any disclaimer, the term of this patent is extended or adjusted under 35 U.S.C. 154(b) by 687 days.

(21) Appl. No.: 11/477,811

(22) Filed: Jun. 30, 2006

(65) Prior Publication Data
US 2007/0012957 A1 Jan. 18, 2007

(30) Foreign Application Priority Data
Jul. 1, 2005 (GB) ................................. 0513631.2

(51) Int. Cl.
G01N 27/26 (2006.01)
G01N 27/31 (2006.01)
G01N 27/40 (2006.01)
H01M 4/02 (2006.01)
H01M 4/04 (2006.01)

(52) U.S. Cl. ....................... 204/431; 204/415; 29/592.1; 29/874; 29/875; 29/890; 502/101

(58) Field of Classification Search ................. 204/415, 204/416, 418, 419, 424, 431, 435, 283, 284, 204/294; 205/779.5, 780.5, 781, 783, 786, 205/789, 794.5; 29/592.1, 874, 875, 890; 502/101
See application file for complete search history.

(56) References Cited

U.S. PATENT DOCUMENTS

| 6,267,866 | B1 * | 7/2001 | Glesener et al. .............. 205/450 |
| 6,584,827 | B2 * | 7/2003 | Kiesele et al. .............. 73/31.05 |
| 2005/0110024 | A1 * | 5/2005 | Swain et al. .................. 257/77 |
| 2005/0224363 | A1 * | 10/2005 | Saha et al. .................. 205/465 |

FOREIGN PATENT DOCUMENTS

WO   WO 03/066930 A1   8/2003
WO   WO 2005/090954 A1   9/2005

OTHER PUBLICATIONS

Yu. V. Pleskov, "Synthetic Diamond, a New Electrode Material for Electroanalysis", Journal of Analytical Chemistry, vol. 55, No. 11, 2000, pp. 1045-1050. Translated from Zhurnal Analiticheskoi Khimii, vol. 55, No. 11, 2000, pp. 1165-1171.

* cited by examiner

*Primary Examiner*—Bruce F Bell
(74) *Attorney, Agent, or Firm*—Nixon & Vanderhye P.C.

(57) ABSTRACT

Disclosed is a gas permeable electrode comprising an electrocatalyst which is permeable to a reactant or reaction product, the electrocatalyst comprising particulate boron-doped diamond. There is also disclosed a method of making an electrocatalyst which is permeable to a reactant or reaction product, the method comprising the step of forming an electrocatalyst comprising particulate boron-doped diamond.

16 Claims, 5 Drawing Sheets

ELECTRODE AND METHOD FOR MAKING ELECTRODE

FIELD OF THE INVENTION

The present invention relates to electrodes for electrochemical uses, and methods of making electrodes. The electrodes are particularly useful for applications where it is desirable for a chemical species, such as an analyte, a reactant or a reaction product, to be able to penetrate or leave the electrode.

BACKGROUND TO THE INVENTION

Within this description and the attached claims, the term catalyst includes any substance which, when added to a reaction mixture, changes the rate of attainment of equilibrium in the system without itself undergoing a permanent chemical change. The term catalyst includes substances which might be changed physically during the reaction they catalyse but which could in theory be recovered chemically unchanged at the end of the reaction. The term electrocatalyst refers to an electrochemically active catalyst.

There are some applications where it is desirable for a chemical species to be able to penetrate or leave an electrode. For example, electrochemical gas sensors are well known. In one configuration, working, counter and reference electrodes are connected through a potentiostatic circuit which maintains a bias potential between the working and reference electrodes. A gas to be measured penetrates the working electrode and undergoes a catalytic reaction. For example, in the case of oxidation of NO, $$NO + H_2O \leftrightarrows NO_2 + 2H^+ + 2e^-$$

A reduction occurs on the counter electrode:

$$\tfrac{1}{2}O_2 + 2H^+ + 2e^- \leftrightarrows H_2O$$

Similar principles apply to electrochemical sensors for measuring liquid analytes.

It is also well known to use an electrode in an electrochemical cell to generate a gas, such as chlorine, or to carry out an electrochemical reaction which consumes a gas. The necessary high reaction rates can be obtained where an electrode is permeable and a higher catalytic surface area is made available. For example, the following working electrode reaction can be used to generate chlorine:

$$2Cl^- \rightarrow Cl_2 + 2e^-$$

On the other electrode:

$$2H^+ + 2e^- \rightarrow H_2$$

It has been known for some time to form an electrode for electrochemical uses by coating a conductive metal with boron-doped diamond. For example, U.S. Pat. No. 6,267,866 discloses an electrode for electrochemical uses made of a conductive metal mesh coated with boron-doped diamond. Boron-doped diamond has desirable electrochemical properties, such as a wide potential window. That is to say, boron-doped diamond can be used as a catalyst at high anodic or cathodic potentials without itself undergoing degradation and without electrochemically oxidising or reducing common solvents such as water. Although boron-doped diamond is an acceptable electrocatalyst for gases such as nitric oxide and ammonia, it is a very poor electrocatalyst for water oxidation or reduction. This advantage allows selective oxidation or reduction of a gas at electrochemical potentials where competing reactions are not favoured. However, known boron-doped diamond coated electrodes include an impervious layer of boron-doped diamond overlaying a conductive metal electrode.

An aim of the present invention is to provide an electrode comprising boron-doped diamond which is permeable to a reactant or reaction product.

SUMMARY OF THE INVENTION

According to a first aspect of the present invention there is provided a gas permeable electrode comprising an electrocatalyst which is permeable to a reactant or reaction product, the electrocatalyst comprising particulate boron-doped diamond.

By using an electrocatalyst comprising particulate boron-doped diamond, we have obtained an electrode which is permeable to a reactant or reaction product.

Preferably, the electrode is for catalysing a reaction in which either or both of a reactant or a reaction product is a gas, and the electrode further comprises gas diffusion means to enable a gas to penetrate or leave (as appropriate) the electrocatalyst.

Preferably, the gas diffusion means comprises a material which is permeable to gas but impermeable to electrolyte.

Preferably, the gas diffusion means comprises a hydrophobic material, intimately mixed with the boron-doped diamond, such that the resulting mixture of boron-doped diamond and hydrophobic material is permeable to gas but impermeable to electrolyte. A suitable hydrophobic material is microporous PTFE (e.g. ICI Fluon). The hydrophobic material is preferably particulate, such as particulate microporous PTFE. The gas diffusion means may also comprise a sheet or strand of material which supports the boron-doped diamond and hydrophobic material and is also permeable to gas but impermeable to electrolyte.

The gas diffusion means may comprise a sheet or strand of material which is permeable to gas and impermeable to electrolyte, to which the particulate boron-doped diamond is bonded.

Preferably, the boron-doped diamond particles comprise diamond doped with between $10^{19}$ and $10^{21}$ boron atoms per cubic centimeter. More preferably, the boron-doped diamond particles comprise diamond doped with the order of $10^{20}$ boron atoms per cubic centimeter.

The boron-doped diamond particles are preferably between 0.1 and 50 microns in diameter, more preferably 1 to 10 microns in diameter. Most preferably, the particles have a diameter of approximately 2 microns. This size range is suitable for use with the electrode manufacturing process described below. The particles do not need to be homogenous in size.

The invention also extends to an electrochemical cell comprising a working electrode, the working electrode being an electrode according to the first aspect. The electrochemical cell may be an electrochemical gas sensor for sensing a gaseous analyte and the electrocatalyst may be permeable to the analyte.

According to a second aspect of the present invention there is provided a method of making an electrocatalyst which is permeable to a reactant or reaction product, the method comprising the step of forming an electrocatalyst comprising particulate boron-doped diamond.

The particular boron-doped diamond is preferably obtainable by (preferably obtained by) chemical vapour deposition. The particulate boron-doped diamond may be obtainable by (preferably obtained by) forming boron-doped diamond using chemical vapour deposition in a reactor under conditions where particles of the above dimensions are formed in the gas phase.

The particulate boron-doped diamond may be obtainable by (preferably obtained by) using chemical vapour deposition to deposit a boron-doped diamond layer onto a substrate, releasing the layer which is formed, and then grinding the resulting boron-doped diamond.

Chemical vapour deposition is preferably metal-organic chemical vapour deposition.

The particular boron-doped diamond may be obtainable by (preferably obtained by) a high-pressure, high-temperature diamond formation technique and then ground.

Preferably, the particulate boron-doped diamond is brought into contact with gas diffusion means which is permeable to gas but impermeable to electrolyte.

The step of bringing the particulate boron-doped diamond into contact with gas diffusion means may comprise forming a layer comprising the particulate boron-doped diamond on a sheet or strand of material which is permeable to gas but impermeable to electrolyte.

The step of bringing the particulate boron-doped diamond into contact with gas diffusion means may comprise the step of intimately mixing the particulate boron-doped diamond with a hydrophobic material. The step of bringing the particulate boron-doped diamond into contact with gas diffusion means may comprise the step of mixing the particulate boron-doped diamond with a particulate material which is permeable to gas but impermeable to electrolyte. The resulting electrocatalyst may be formed as a layer on a sheet or strand of material which is permeable to gas but impermeable to electrolyte.

According to a third aspect of the present invention, there is provided a process for making a gas permeable electrode comprising the steps of making an electrocatalyst according to the second aspect of the present invention and forming a gas permeable electrode comprising the electrocatalyst.

According to a fourth aspect of the present invention, there is provided a method of making an electrochemical cell comprising the step of making a gas permeable electrode according to the method of the second aspect. There is also provided a method of making an electrochemical gas sensor, comprising the step of making a gas permeable working electrode according to the method of the second aspect.

BRIEF DESCRIPTION OF THE DRAWINGS

The invention will be further described, by way of illustration, with reference to the accompanying drawings, in which.

DETAILED DESCRIPTION OF AN EXAMPLE EMBODIMENT

An electrocatalyst comprising particulate boron-doped diamond which is permeable to a reactant or reaction product can be made as follows:

Boron-doped diamond grit with a typical particle size of 2 microns diameter and a level of doping of at least $10^{20}$ boron atoms per cubic centimeter can be made by high pressure, high temperature growth in a press and then ground to 2 microns particle size. The concentration of boron atoms is not critical and is not tightly controlled. Boron-doped diamond grit with these properties is available from Element Six (UK) Ltd. of Maidenhead, United Kingdom.

Firstly, 1.0 g of boron-doped diamond is added to a 1.8 ml solution of 1.4% isooctylphenoxypolyethoxyenthanol (Triton X) solution in water. Thereafter, 0.15 ml of PTFE in aqueous dispersion (Fluon GP1 brand) is added thereto and the components are mixed by sonication (10 minutes) and stirred with a magnetic stirrer bar. Triton X is available from BDH (Poole, United Kingdom) and Fluon GPl is distributed by Whitford Plastics Ltd., Runcorn, United Kingdom (Triton X and Fluon are Trade Marks).

The resulting slurry is then drawn up into a pipette, and 50 microliters is dispensed in to a circular depression on an electrode forming mould. The mould comprises disc shaped depressions of 13 mm diameter over a pressable member. The electrocatalyst is spread throughout the disc with the pipette, as evenly as possible.

The resulting cakes of electrocatalyst are then dried for 60 minutes at 60 C, followed by a further 30 minutes at 150 C9 then 15 minutes at 280 C. A membrane disc, of gas porous hydrophobic PTFE, such as Zytex, Goretex or Mupor (Zytex, Goretex and Mupor are Trade Marks) is placed on top of the press. A baked electrocatalyst disc from the previous step is then placed on top of the membrane, with the cake side facing down, and the electrocatalyst cake and electrode disc being lined up coaxially. Next, a mechanical press applies pressure to the pressable member, thereby pressing the electrocatalyst into the PTFE membrane.

Thereafter, the press and mould can be removed revealing the electrocatalyst cake.

Figure 1:
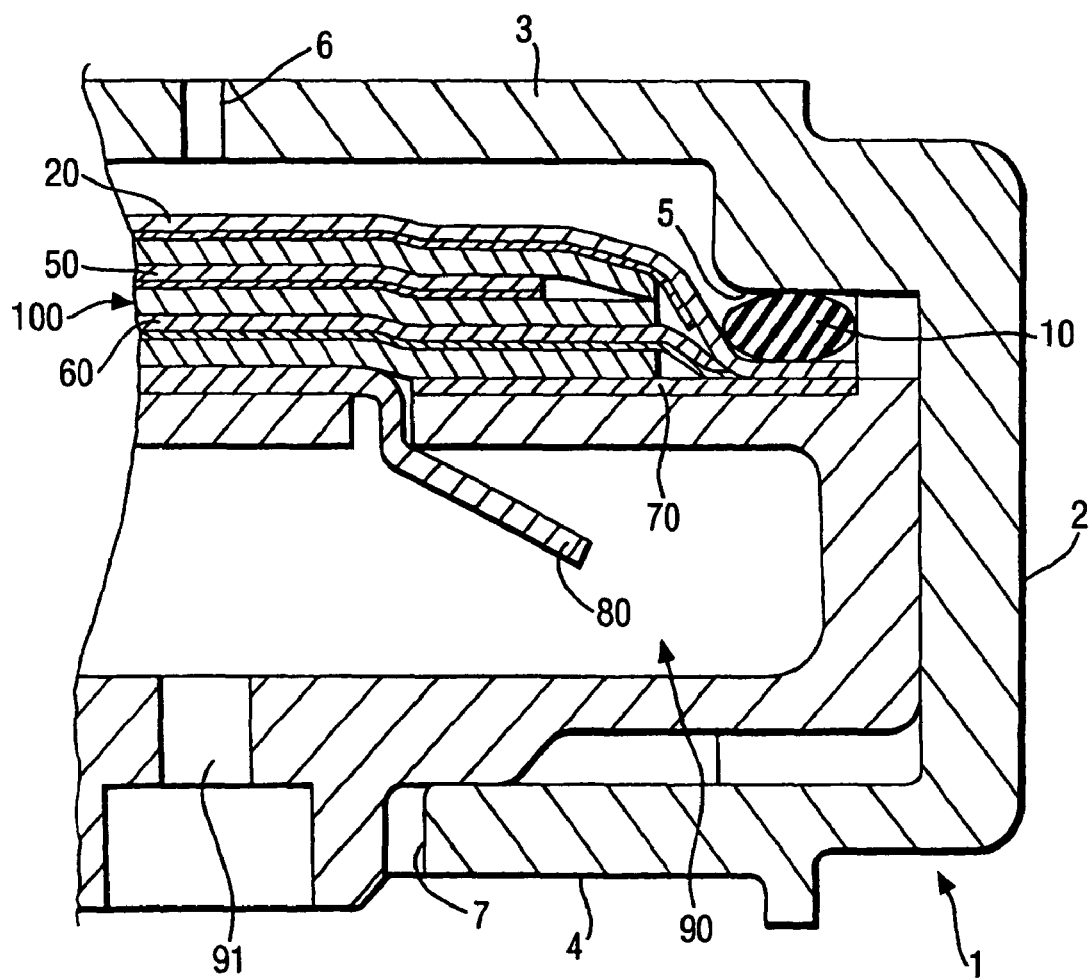
FIG. 1 is a sectional view of one embodiment of an assembled nitric oxide sensor in accordance with the invention.
Figure 2:
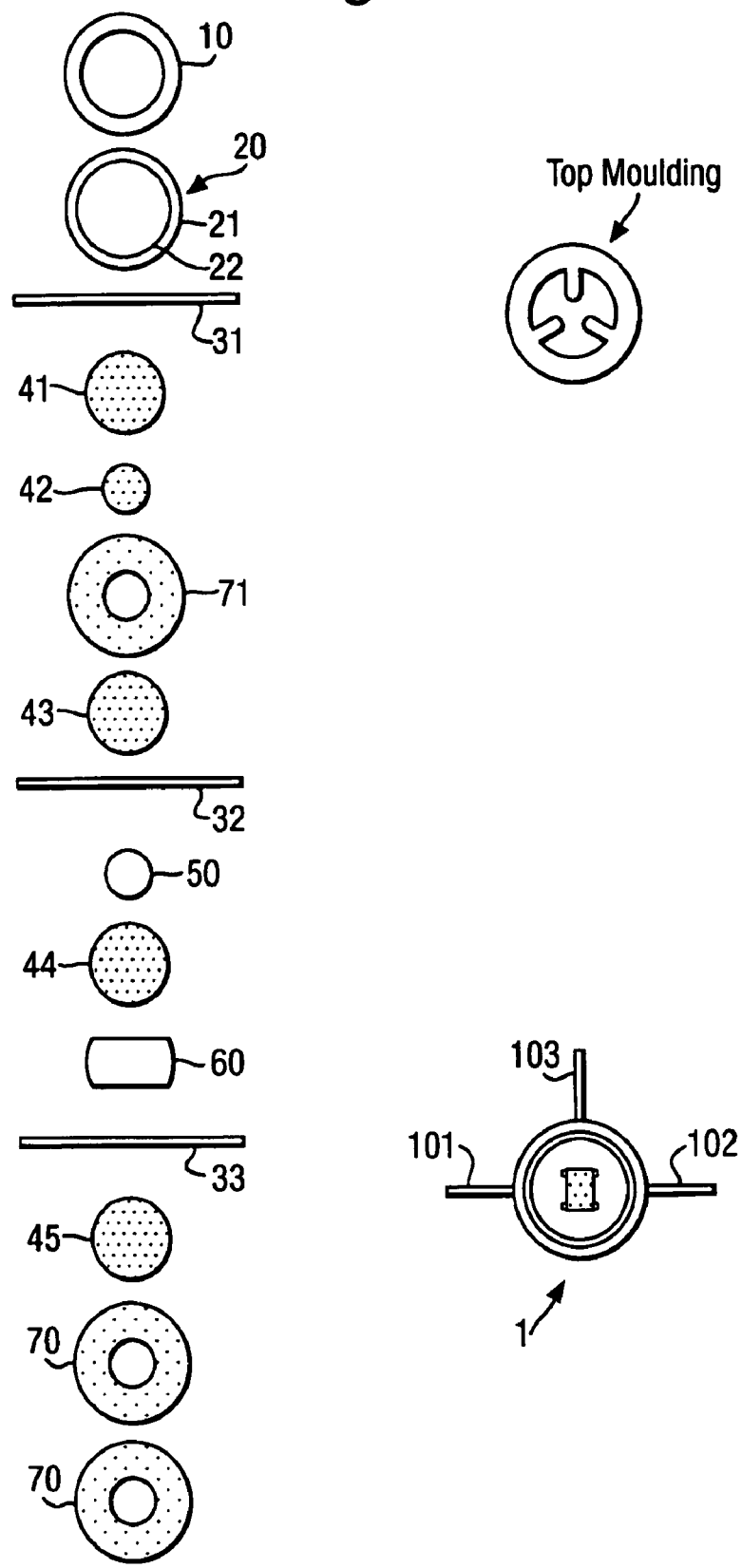
FIG. 2 is an exploded view of an electrode stack assembly for the electrochemical sensor of FIG. 1.

One preferred embodiment of a sensor in accordance with the invention, for measuring nitric oxide or ammonia in a gas sample, is illustrated in FIGS. 1 and 2. FIG. 1 is slightly simplified, with some of the components shown in FIG. 2 omitted from FIG. 1 for clarity. The physical structure, construction and operation of the sensor are generally known, the novelty lies in the working electrode, discussed above, and the resulting sensor properties.

As shown in FIG. 1, the sensor comprises a generally cylindrical sensor housing or casing 1, made of a corrosion resistant engineering plastic material such as polycarbonate or polysulfone, approximately 25 mm in diameter in which is housed an electrolyte reservoir 90 made of polysulfone or polycarbonate, an electrode stack assembly 100 and a wick 80 of unbound glass fibre, a hydrophilic non-conductive electrolyte transporting material which functions as a wick, extending into the reservoir 90 for contact with electrolyte therein. Sensor casing 1 has a cylindrical side wall 2 and generally planar circular top and bottom walls, 3 and 4, respectively. The top wall 3 has a stepped configuration and includes an annular shoulder portion S around the periphery. A central circular opening 6 passes through the top wall 3 which functions to permit gas passage to the interior of the casing whilst acting as a means to restrict the diffusion of the gas sample to the working electrode, discussed below. The circular opening 6 is referred to as the capillary. In the present example, the capillary is 4 mm diameter. The bottom wall 4 includes a larger central circular opening 7 through which protrudes part of the reservoir 90, this part including a suitable opening 91 to enable supply of electrolyte to the reservoir, during manufacture.

The casing 1 is conveniently of two-part construction (not shown) for assembly purposes. The electrode stack 100 is further illustrated in FIG. 2. In FIG. 2, the relative dimensions of the various components are as shown. The components of the electrode stack are generally of planar or sheet-like form, generally being of circular or annular configuration as shown in FIG. 2.

Working from the bottom up as shown in FIG. 2, electrode stack 100 comprises two annular stack bases 70 of gas porous hydrophobic PTFE polymer material in the form of Zytex, Goretex or Mupor (Zytex, Goretex and Mupor are Trade Marks). (Only one stack base is shown in FIG. 1). These are followed by a circular separator disc 45 made of unbound glass fibre which is a hydrophilic, non-conductive material permeable to the electrolyte which functions to wick electrolyte. Then follows a platinum strip or rod 33 (not shown in FIG. 1) that functions as an electrical conductor for connection to a first terminal pin 101 on the sensor housing. The assembly then includes a counter electrode 60 that is generally rectangular in plan.

Counter electrode 60 comprises an electocatalytic layer covering the full extent of the downward facing side of a hydrophobic microporous PTFE support (e.g. of Zytex, Goretex or Mupor). The electrocatalytic layer is formed from a mixture of Platinum oxide (Johnson Matthey) and PTFE binder sintered at elevated temperature to give a porous binder/catalyst material that can be bonded to the support.

The stack then includes a further separator disc 44 similar to separator disc 45. Next in the assembly is circular reference electrode 50 of similar materials and construction as the counter electrode 60 and comprising a Platinum oxide (Johnson Matthey)/PTFE electrocatalytic layer covering the downward facing side of a hydrophobic microporous PTFE support. Then follows a second platinum strip 32 similar to strip 33 and leading to a second terminal pin 102. A third separator disc 43 similar to discs 45 and 44 is then provided, followed by a further gas porous PTFE ring 71, similar to stack base 70 and having a smaller separator disc 42, which is similar to discs 43, 44 and 45 in all but size. Thereafter, a further separator disc 41, similar to disc 45 is provided followed by a third platinum strip 31, similar in construction and function to strips 33 and 32 and leading to a third terminal pin 103.

(Items 71, 42 and 41 and platinum strips 31 are not shown in FIG. 1).

Finally, the electrode assembly includes a circular working electrode 20. The working electrode 20 includes a boron-doped diamond/PTFE electrocatalytic layer on the circular central portion only of the downward facing surface of a hydrophobic microporous PTFE support. The manufacturing of the boron-doped diamond/PTFE electrocatalytic layer is discussed above. In the present example, the electrocatalytic portion of the working electrode 20 is 13 mm in diameter.

The components of the electrode stack assembly are assembled in order on the reservoir 90 and wick 80 with the electrocatalytic layers on the undersides of the associated supports, facing downwardly towards the reservoir as shown in FIG. 1. An "O" ring 10 is located on top of the assembly, being sized to contact the outer periphery of the working electrode support 21. On insertion of the assembly into the casing 1, as shown in FIG. 1, the casing shoulder 5 contacts the "O" ring 10 which urges the working electrode support 21 into contact with the outer periphery of the stack base 70 and forms a seal, also bringing the various electrode stack components into close contact as shown. During this assembly some of the electrode stack components deform from their initially planar condition, but such components are still to be considered as of planar configuration.

5 Molar sulfuric acid electrolyte is located in the chamber within reservoir 90 for contact with wick 80. The reservoir is not filled completely with electrolyte, leaving a free volume in the reservoir to allow for the possibility of water absorption resulting in an increase in the electrolyte volume, or for water loss through evaporation past the working electrode 20, reducing electrolyte volume. The reservoir may include hydrophilic non-conductive wicking or wetting material to provide a continuous electrolyte path from the reservoir to the separator discs.

The electrode supports are all made from hydrophobic microporous PTFE. The stack base 70 is made from PTFE. The hydrophobic properties of the material mean it is impermeable to the electrolyte so that electrolyte is effectively sealed within the housing by virtue of the seal between stack base 70 and the working electrode support 21 produced by "O" ring 10.

Figure 3:
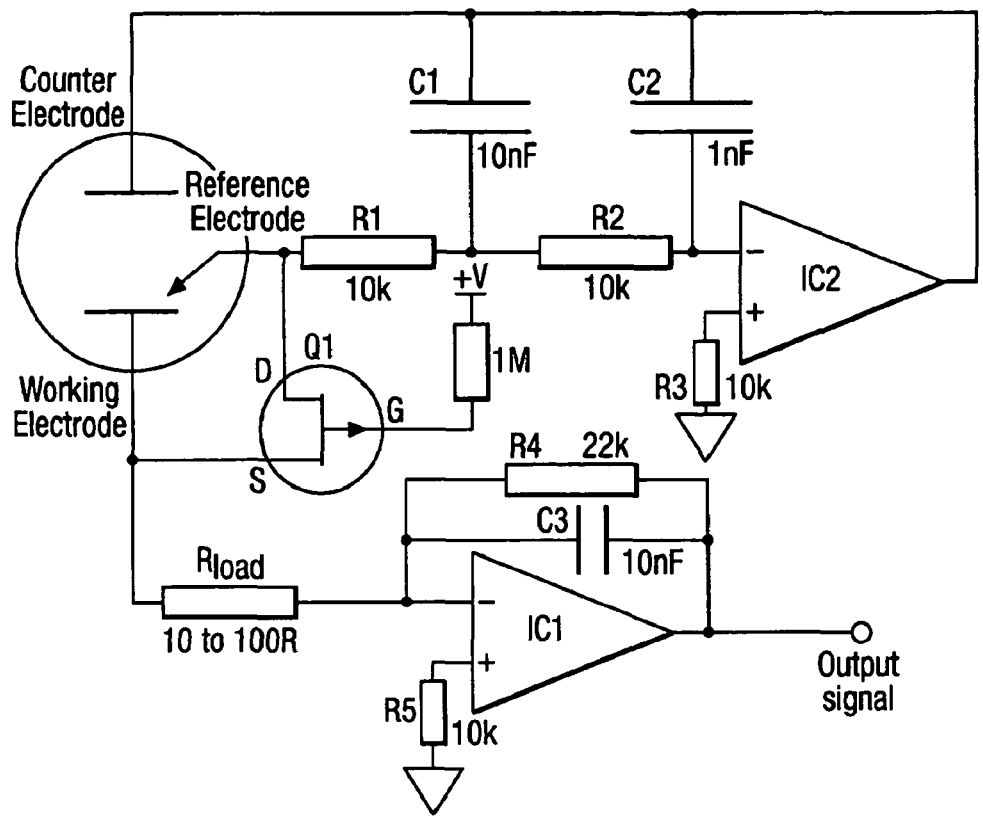
FIG. 3 is a circuit diagram of a standard potentiostatic circuit, suitable for use with the electrochemical sensor of the present invention.
Figure 4:
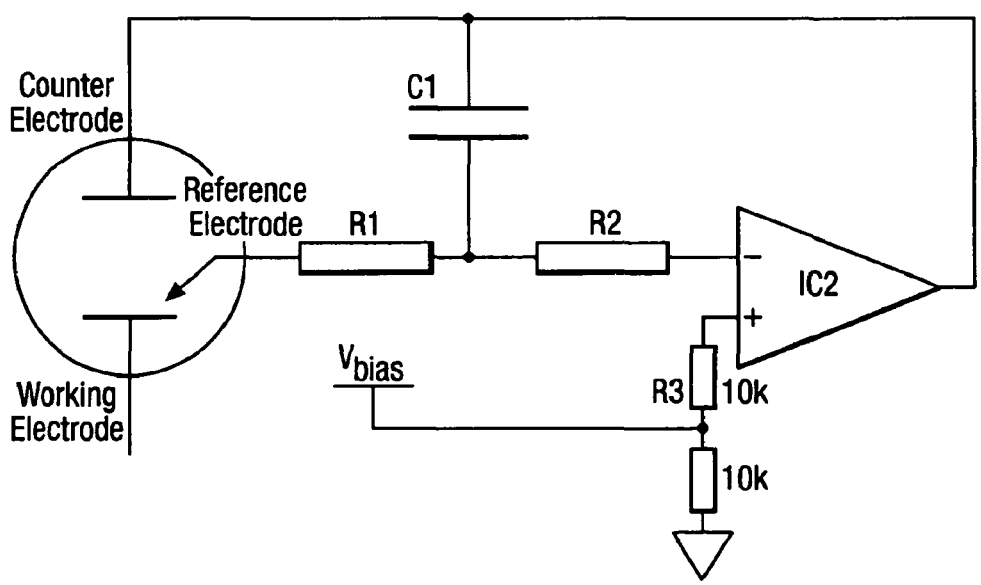
FIG. 4 is a variant of part of the circuit diagram of FIG. 3, for applying a bias potential between the working and reference electrodes of a nitric oxide or ammonia sensor.

Before use, the sensor is assembled, and then the sensor is tested and calibrated. In each of these steps, the casing terminal pins are connected to an external potentiostat, which is used in known manner to set the potential difference of the working electrode with respect to the potential of the reference electrode. An example potentiostat circuit which can be used to operate the electrochemical sensor of the present invention is shown in FIG. 3. The reference electrode provides a standard voltage which, in a potentiostatic circuit, sets the working electrode operating potential. An important benefit of the invention is that this potentiostat circuit is a well-known standard, which can readily be optimised by one skilled in the art. FIG. 4 illustrates a conventional modification which enables a bias potential to be applied between the working and reference electrodes. In FIGS. 3 and 4, ICI and IC2 are Operational Amplifiers and Q1 is a depletion mode JFET. Application note AAN 105, available from Alphasense Limited (Great Dunmow, United Kingdom) discusses such circuitry in more depth.

In use, a potentiostat shown in FIG. 4 applies a potential difference (typically 300 mV) between the reference and working electrodes, with the resulting working electrode current being proportional to the concentration of nitric oxide up to over 2000 ppm.

Figure 5:
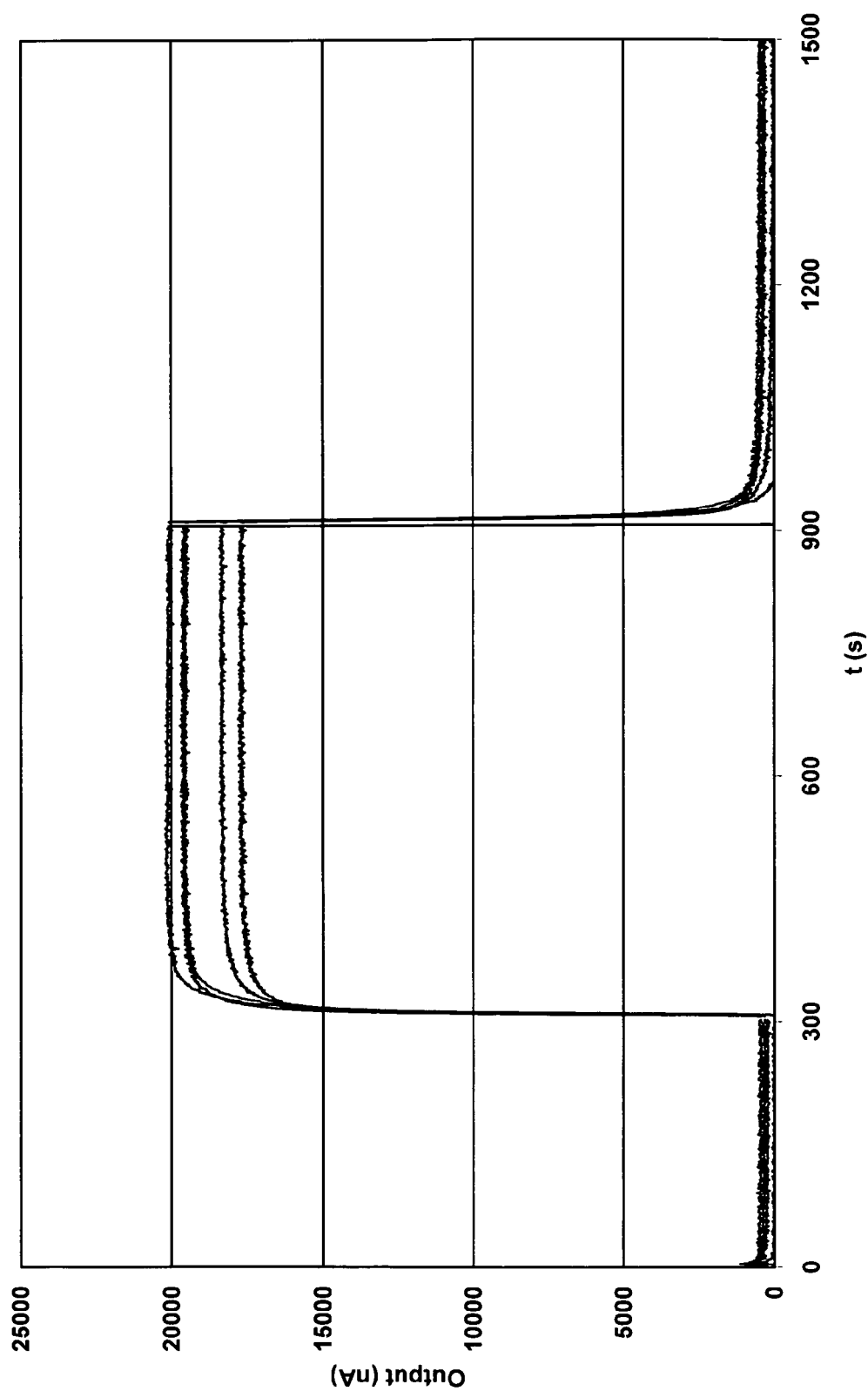
FIG. 5 is a graph showing the working electrode current with time of an electrochemical gas sensor in response to 20 ppm of nitric oxide.

FIG. 5 is a graph showing the resulting working electrode current response with time when the electrochemical gas sensor, with a bias voltage of 300 mV, is brought into contact with 20 ppm of nitric oxide. Clean air without nitric oxide is first passed over the sensor at 0.5 liter/minute flow rate for 5 minutes. Then a gas mixture of 20 ppm nitric oxide and balance nitrogen is passed over the sensor for 5 minutes, also at 0.5 liter/minute. Finally, clean air without nitric oxide is passed over the sensor at the same flow rate. The current generated by the working electrode is measured continuously.

Figure 6:
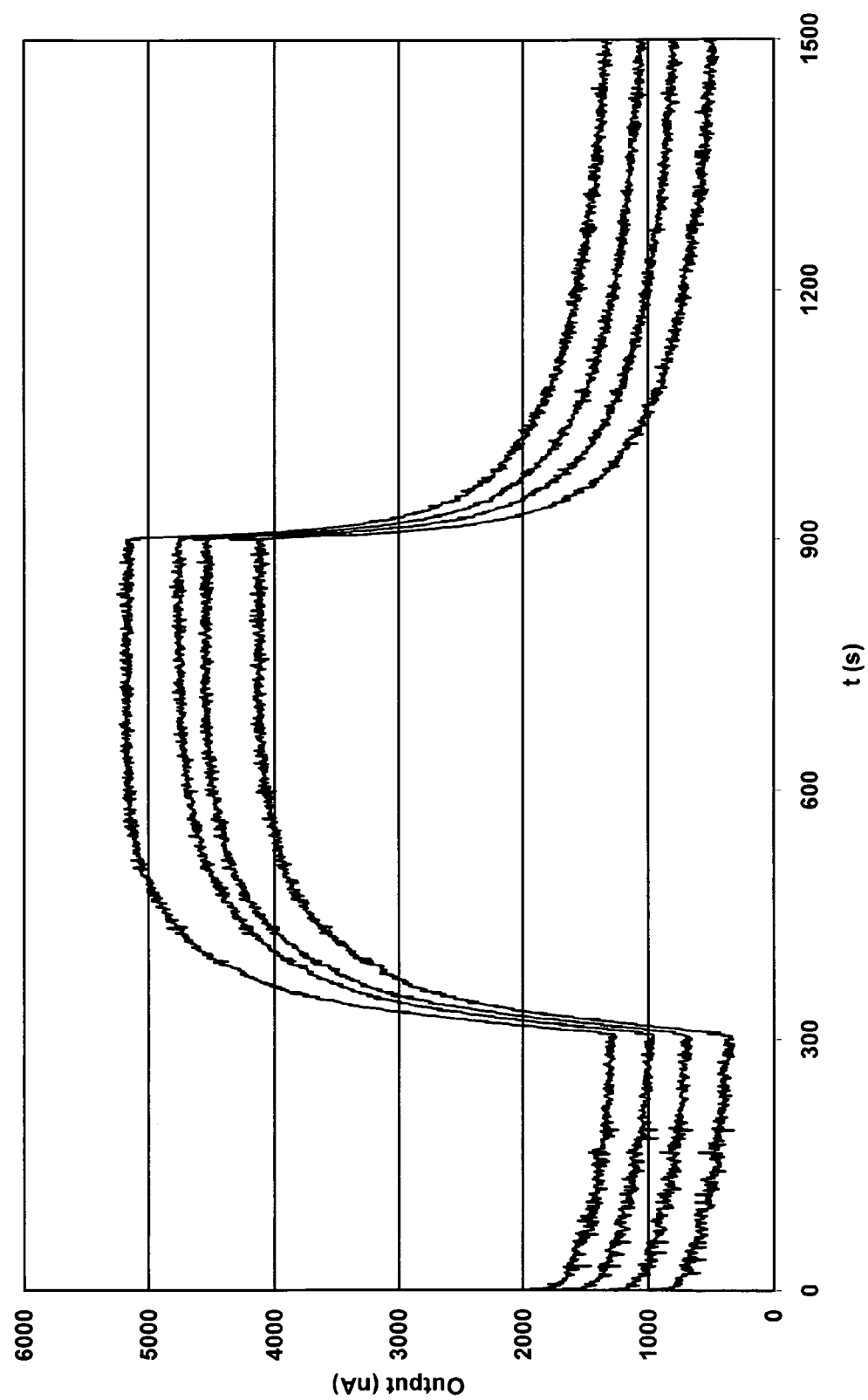
FIG. 6 is a graph showing the working electrode current with time of an electrochemical gas sensor, with a bias of 900 mV, in response to 25 ppm ammonia.

FIG. 6 is a graph showing the resulting working electrode current response with time when the electrochemical gas sensor, with a bias voltage of 900 mV, is brought into contact with 25 ppm ammonia. Clean air without ammonia is first passed over the sensor at 0.5 liter/minute flow rate for 5 minutes. Then a gas mixture of 25 ppm ammonia and balance air is passed over the sensor for 5 minutes, also at 0.5 liter/minute. Finally, clean air without ammonia is passed over the sensor at the same flow rate. The current generated by the working electrode is measured continuously.

Further alterations and modifications may be made within the scope of the invention herein disclosed.

The invention claimed is:

1. An electrochemical gas sensor for sensing a gaseous analyte, comprising a gas permeable working electrode, the gas permeable working electrode comprising an electrocatalyst which is permeable to a reactant or reaction product, the electrocatalyst comprising particulate boron-doped diamond, wherein the electrocatalyst is permeable to the analyte.

2. An electrochemical gas sensor according to claim 1 for catalysing a reaction in which either or both of a reactant or a reaction product is a gas, and the electrode further comprises gas diffusion means to enable a gas to penetrate or leave the electrode catalyst.

3. An electrochemical gas sensor according to claim 1, wherein the gas diffusion means comprises a material which is permeable to gas but impermeable to electrolyte.

4. An electrochemical gas sensor according to claim 3, wherein the gas diffusion means comprises a hydrophobic material, intimately mixed with the particulate boron-doped diamond, such that the resulting mixture of particulate boron-doped diamond and hydrophobic material is permeable to gas but impermeable to electrolyte.

5. An electrochemical gas sensor according to claim 3, wherein the gas diffusion means comprises a particulate material which is permeable to gas but impermeable to electrolyte and which is mixed with the particulate boron-doped diamond.

6. An electrochemical gas sensor according to claim 3, wherein the gas diffusion means comprises a sheet or strand of material which supports the catalyst and hydrophobic material and is also permeable to gas but impermeable to electrolyte.

7. An electrochemical gas sensor according to claim 3 wherein the gas diffusion means comprises a sheet or strand of material which is permeable to gas and impermeable to electrolyte, to which the particulate boron-doped diamond is bonded.

8. An electrochemical gas sensor according to claim 1, wherein the boron-doped diamond particles comprise diamond doped with between $10^{19}$ and $10^{21}$ boron atoms per cubic centimeter of solid.

9. An electrochemical gas sensor according to claim 8, wherein the boron-doped diamond particles comprise diamond doped with the order of $10^{20}$ boron atoms per cubic centimeter.

10. An electrochemical gas sensor according to claim 1, wherein the boron-doped diamond particles are between 0.1 and 50 microns in diameter.

11. A method of making an electrochemical gas sensor, comprising: forming an electrocatalyst which is permeable to a reactant or reaction product, the electrocatalyst comprising particulate boron-doped diamond, wherein particulate boron-doped diamond is obtained by forming boron-doped diamond using chemical vapour deposition to deposit a boron-doped diamond layer onto a substrate, releasing the later which is formed, grinding the resulting boron-doped diamond, and forming a gas permeable electrode comprising the electrocatalyst.

12. A method according to claim 11, wherein the particulate boron-doped diamond is obtained by a high-pressure, high-temperature diamond formation technique and then ground.

13. A method according to claim 11, wherein the particulate boron-doped diamond is brought into contact with a gas diffusion unit which is permeable to gas but impermeable to electrolyte.

14. A method according to claim 13 wherein bringing the particulate boron-doped diamond into contact with the gas diffusion unit comprises forming a layer comprising the particulate boron-doped diamond on a sheet or strand of material which is permeable to gas but impermeable to electrolyte.

15. A method according to claim 13, wherein bringing the particulate boron-doped diamond into contact with the gas diffusion unit comprises intimately mixing the particulate boron-doped diamond with a hydrophobic material.

16. A method according to claim 13, wherein bringing the particulate boron-doped diamond into contact with the gas diffusion unit comprises mixing the particulate boron-doped diamond with a particulate material which is permeable to gas but impermeable to electrolyte.

* * * * *

UNITED STATES PATENT AND TRADEMARK OFFICE
CERTIFICATE OF CORRECTION

PATENT NO.         : 7,790,005 B2
APPLICATION NO.    : 11/477811
DATED              : September 7, 2010
INVENTOR(S)        : Dawson et al.

It is certified that error appears in the above-identified patent and that said Letters Patent is hereby corrected as shown below:

On the Title Page

Delete Item "(73) Assignee: ELEMENT SIX LIMITED" and insert

Item --(73) Assignee: ALPHASENSE LIMITED--.

Signed and Sealed this
Sixth Day of December, 2011

David J. Kappos
*Director of the United States Patent and Trademark Office*